United States Patent
Twardowski

(10) Patent No.: US 6,592,565 B2
(45) Date of Patent: Jul. 15, 2003

(54) PATIENT-TAILORED, CENTRAL-VEIN CATHETERS

(76) Inventor: Zbylut J. Twardowski, 304 Devine Ct., Columbia, MO (US) 65203

(*) Notice: Subject to any disclaimer, the term of this patent is extended or adjusted under 35 U.S.C. 154(b) by 92 days.

(21) Appl. No.: 09/844,578

(22) Filed: Apr. 26, 2001

(65) Prior Publication Data

US 2003/0023198 A1 Jan. 30, 2003

(51) Int. Cl.$^7$ ............................................. A61M 31/00
(52) U.S. Cl. ..................................... 604/500; 604/175
(58) Field of Search ................................. 604/174, 175, 604/523, 117, 19, 500, 264, 508; 128/898

(56) References Cited

U.S. PATENT DOCUMENTS

| | | | |
|---|---|---|---|
| 4,489,387 A | * 12/1984 | Lamb et al. ................ 600/301 |
| 4,936,826 A | 6/1990 | Amarasinghe |
| 5,057,075 A | 10/1991 | Moncrief et al. |
| 5,098,413 A | 3/1992 | Trudell et al. |
| 5,141,499 A | 8/1992 | Zappacosta |
| 5,156,597 A | 10/1992 | Verreet et al. |
| 5,171,227 A | 12/1992 | Twardowski et al. |
| 5,209,723 A | 5/1993 | Twardowski et al. |
| 5,308,338 A | 5/1994 | Helfrich |
| 5,405,320 A | 4/1995 | Twardowski et al. |
| 5,509,897 A | 4/1996 | Twardowski et al. |
| 5,685,867 A | 11/1997 | Twardowski et al. |
| 6,074,367 A | * 6/2000 | Hubbell ..................... 206/364 |

OTHER PUBLICATIONS

Steinberg et al., Measurements of Central Blood Vessels in Infants and Children: Normal Values, Catheterization and Cardiovascular Diagnosis 27:197–201 (1992).*

Z.J. Twardowski, R.M. Seger "Dimensions of central venous structures in humans measure in vivo using magnetic resonance imaging: Implications for central–vein catheter dimensions"; The International Journal of Artificial Organs/ vol. 25/No. 2, 2002/ pp. 107–123.

Z.J. Twardowski, J.D. Haynie Measurements of hemodialysis catheter blood flow in vivo; The International Journal of Artificial Organs; vol. 25/No. 4, 2002/ pp. 276–280.

Shaldon et al, Haemodialysis by Percutaneous Catheterisation of the Femoral Artery and Vein with Regional Heparinisation, Oct. 14, 1961, The Lancet; 2:857–859.

Robert Aubaniac, L'injection intraveineuse sous–claviculaire, Atvantes et technique, Oct. 25, 1952, Le Presse Medicale; 60: 1456.

Wilson et al, Central Venous Pressure in Optimal Blood Volume Maintenance, Feb. 21–24, 1962, Arch Surg 1962; 85:563–578.

(List continued on next page.)

*Primary Examiner*—Henry C. Yuen
*Assistant Examiner*—Patrick Buechner
(74) *Attorney, Agent, or Firm*—Garrettson Ellis Seyfarth Shaw

(57) ABSTRACT

The method of selecting and implanting a permanent venous catheter into a patient for use in chronic, extracorporeal blood treatment procedures. The method comprises determining the Body Surface Area of the patient. One then selects a permanent venous catheter having an actual length which is within 10% of a desired length as indicated in a Table found in this application for the Body Surface Area of the particular patient and a particular vein through which the catheter is to extend. Also, the internal diameter of the tubing is preferably adjusted in a manner correlating with the catheter length. Following catheter selection, the venous catheter is implanted in the venous system of the patient with the distal tip of the catheter being in or adjacent to the upper right atrium of the heart.

18 Claims, 2 Drawing Sheets

OTHER PUBLICATIONS

Christensen et al, Complications of Percutaneous Catheterization of the Subclavian Vein in 129 Cases, Feb. 17, 1967, Acta Chir Scand 133:615–620.

Schapira et al, Hazards of Subclavian Vein Cannulation for Central Venous Pressure Monitoring, Jul. 31, 1967, JAMA, vol. 201, No. 5: 111–113.

Rams et al, A Simple Method for Central Venous Pressure Measurements, Jun. 1966, Arch Surg— vol. 92; 92:886.

Erben et al, Experience with Routine use of Subclavian Vein Cannulation in Haemodialysis, Proc Eur Dial Transpl Assoc 1969; 6: 59–64.

Seldinger SI, Catheter Replacement of the Needle in Percutaneous Arteriography, A New Technique, Acta Radiol 1953; 39:368–376.

Uldall et al, A Subclavian Cannula for Temporary Vascular Access for Hemodialysis or Plasmapheresis, Oct. 1979, Dialysis & Transplantation, vol. 8, No. 10; 963–968.

DeCubber et al, Single Needle Hemodialysis with the Double Headpump via the Subclavian Vein, Dec. 1978, Dialysis & Transplantation, vol. 7, No. 12; 1261–1263.

Hermosura et al, Measurement of Pressure During Intravenous Therapy, JAMA, Jan. 24, 1966, vol. 195, No. 4; 181 (321).

Bregman et al, The Double–Lumen Subclavian Cannula—A Unique Concept in Vascular Access, Dialysis & Transplantation, vol. 11, No. 12; Dec. 1982; 1065–1070.

Graber et al, The Quinton–Mahurkar Dual Lumen Subclavian Catheter—Preliminary Clinical Evaluation, Dialysis & Transplantation, vol. 12, No. 12; Dec. 1963; 847–850.

Mahan et al, The Hickman Catheter: A new hemodialysis access device for infants and small children, Kidney International, vol. 24; 1983; 694–697.

Francis et al, Right–Atrial Catheters for Long–term Vascular Access in Haemodialysis Patients, The Lancet, Aug. 7, 1982; 301–302.

Sanders et al, Experience with Double Lumen Right Atrial Catheters, Apr. 1982 Journal of Parenteral and Enteral Nutrition, vol. 6, No. 2, 95–99.

Schanzer et al, Double Lumen, Silicone Rubber, Indwelling Venous Catheters: A new modality for angioacess, Arch Surg Feb. 1986; 121: 229–232.

Schwab et al, Prospective Evaluation of A Dacron Cuffed Hemodialysis Catheter for Prolonged Use, American Journal of Kidney Diseases, vol. XI, No. 2, Feb. 1988; 166–169.

Moss et al, Use of Silicon Catheter with a Dacron Cuff for Dialysis Short–Term Vascular Access, American Journal of Kidney Diseases, vol. XII, No. 6, 1988; 492–498.

Carbone, V, Hemodialysis Using the PermCath™ Double Lumen Catheter, ANNA Journal, Jun. 1988, vol. 15, No. 3; 171–173 & 193.

Twardowski, ZJ, Percutaneous Blood Access for Hemodialysis, Seminars in Dialysis, vol. 8, No. 3, May–Jun. 1995; 175–186 (320–331).

Canaud et al, Access vasculaire temporaire: du peripherique au central, due temporarie au permanent, Nephrologie vol. 15, No. 2, 53–59, 1994.

Tesio et al, Double Catheterization of the Internal Jugular Vein for Hemodialysis: Indications, Techniques, and Clinical Results, Artificial Organs, 1994; 18(4):301–304.

Tesio et al, Successful Long–Term Central Venous Access, Home Hemodialysis International, vol. 2, 1998; 38–40.

Twardowski et al, All Currently Used Measurements of Recirculation in Blood Access by Chemical Methods are Flawed due to Intradialytic Disequilibrium or Recirculation at Low Flow, American Journal of Kidney Diseases, vol. 32, No. 6, Dec. 1998; 1–14.

Canaud et al, Internal Jugular Vein Cannulation with Two Silicone Rubber Catheters: A New and Safe Temporary Vascular Access for Hemodialysis. Thirty Months' Experience, Artificial Organs, 1986 10(5): 397–403.

Canaud et al, Internal Jugular Vein Cannulation Using 2 Silastic Catheters. A New, Simple and Safe Long–Term Vascular Access for Extracorporeal Treatment, Nephron 43: 133–138 (1986).

Welch et al, The Role of Catheter Composition in the Development of Thrombophlebitis, Surgery, Gynecology & Obstetrics, Mar. 1974, vol. 138: 421–424.

Ratcliffe et al, Massive Thrombosis Around Subclavian Cannulas Used for Haemodialysis, Lancet Jun. 26, 1982; 1:1472–1473.

Hoshal et al, Fibrin Sleeve Formation on Indwelling Subclavian Central Venous Catheters, Arch Surg. vol. 102, Apr. 1971; 353–358.

Cimochowski et al, Superiority of the Internal Jugular over the Subclavian Access for Temporary Dialysis, Nephron, 1990; 54:154–161.

Schillinger et al, Post Catheterisation Vein Stenosis in Haemodialysis: Comparative Angiographic Study of 50 Subclavian 50 Internal Jugular accesses, Nephrol Dial Transplant (1991) 6:722–724.

Twardowski ZJ, High–Dose Intradialytic Urokinase to Restore the Patency of Permanent Central Vein Hemodialysis Catheters, American Journal of Kidney Diseases, vol. 31, No. 5 (May), 1998: 841–847.

Maartin et al, TPN Catheter Sepsis: Lack of Effect of Subcutaneous Tunnelling of PVC Catheters on Sepsis Rate, Journal of Parenteral and Enteral Nutrition, vol. 4, No. 5, 1980: 514–517.

Rovner et al, Comparison of Cuffed vs. Uncuffed Catheters for Extracorporeal Therapy in Pediatric Patients, Dialysis & Transplantation, vol. 21, No. 8, Aug. 1992: 513–522.

U.S. Renal Data System, USRDS 1992 Annual Data Report, VI. Catheter–Related Factors and Peritonitis Risk in CAPD Patients, Am J Kidney Dis 1992; vol. XX, No. 5 (Suppl 2): 48–54.

Twardowski et al, Six–year Experience with Swan Neck Presternal Peritoneal Dialysis Catheter. Abstracts of the XXXth Annual Meeting San Antonio, Texas, Nov. 2–5, 1997, Journal of the American Society of Nephrology 1997, vol. 8:183A.

Shaldon, Percutaneous Vessel Catherization for Hemodialysis, 17–19, ASAIO Journal 1994.

\* cited by examiner

PATIENT-TAILORED, CENTRAL-VEIN CATHETERS

BACKGROUND OF THE INVENTION

Jugular and subclavian catheters are intended as a permanent blood access for fluid delivery into the blood stream or egress of blood. Although these catheters may be used for various purposes including treatment of acute renal failure, they are essentially intended for treatment of chronic renal failure. The invention will decrease the rates of thrombosis and infections and prolong the overall survival of the catheters.

There are numerous manufacturers producing various implantable catheters, and the line of products is changing every year. An extensive review of all available catheters for acute and chronic hemodialysis was published in 1995 (Twardowski ZJ: Percutaneous blood access for hemodialysis. Seminars in Dialysis 1995; 8: 175–186).

Dual Lumen Catheters

These catheters are made of silicone rubber or polyurethane. Silicone rubber is less thrombogenic than polyurethane. Polyurethane is thermoplastic, while silicone rubber is thermoset and does not soften at body temperature. Depending on the manufacturing process, the silicone rubber catheter may be made softer or harder, but is usually made soft. Most currently used catheters have dual lumens and are provided with a single polyester cuff. Most dual-lumen catheters have a beveled inflow bore and a few side holes for inflow. Almost all catheters are radiopaque or are provided with radiopaque stripe.

The catheters are inserted transcutaneously through the subclavian or jugular veins using a peel-away sheath method or surgically through the jugular vein into the superior vena cava or right atrium. Femoral veins are usually not used as a long-term access for hemodialysis. Jugular veins serve as a primary insertion site, because complication rates associated with insertion through the subclavian veins are significantly higher.

Although historically the catheters were inserted with various approaches, currently the catheter is usually inserted through the Sedillot triangle (between the sternal and clavicular heads of the sternocleidomastoid muscle) using the Seldinger (Seldinger SI: Catheter replacement of needle in percutaneous arteriography; new technique. Acta Radiol 1953; 39: 368–376) method. In this method the vein is punctured with a large bore needle and a guide wire is inserted into the vein through the needle. The needle is withdrawn, the skin tunnel is created by a small incision, the entrance into the vein is prepared by a dilator. The subcutaneous tunnel is created with a trocar, the catheter is inserted through the tunnel and introduced into the vein using peel-away sheath. Then the tip of the catheter is advanced through the brachiocephalic vein into the superior vena cava or right atrium. The surgical method is similar, with the exception that the incision over the Sédillot triangle is bigger and the vein is punctured under the direct vision.

There are two method of subcutaneous tunnel creation. Because most catheters have an attached Y extension for connection with the dialyzer lines, the tunnel must be created from the skin exit to the site of the vein puncture (standard tunneling method). Another method, as described in my previous patents (U.S. Pat. Nos. 5,209,723; 5,405,320; and 5,509,897) requires that the catheter be tunneled from the vein puncture site to the exit (reversed tunneling method). Such a method is possible if the Y extension is attached to the catheter after the catheter is pulled through the exit. In both methods the subcutaneous tunnel is created over the clavicle; thus the catheter in the tunnel has more or less a reversed "U" shape.

Mutatis mutandis, an insertion through the subclavian veins is similar to that through the jugular veins. The puncture of the subclavian vein is done just below the clavicle and slightly outside of the midclavicular line.

To prevent blood recirculation, most dual lumen catheters have inflow and outflow bores staggered approximately 2 cm, with outflow bore distal to that of inflow bore. Our studies (Twardowski Z J, Van Stone J C, Haynie J: All currently used measurements of recirculation in blood access by chemical methods are flawed due to intradialytic disequilibrium and/or recirculation at low flow Am J Kidney Dis 1998; 32 (6): 1046–1058.) showed that at the high blood flow (over 300 mL/min) blood recirculation is only moderate, even in catheters with a flush tip. Various tip configurations aiming at decreasing clot formation were patented (U.S. Pat. No. 5,509,897; 5,569,182; and 5,685,867).

Single Lumen Catheters

For subclavian vein catheterization, single lumen catheters were used in 1969 (Erben J, Kvasnicka J, Bastecky J, Vortel V: Experience with routine use of subclavian vein cannulation in haemodialysis. Proc Eur Dial Transpl Assoc 1969; 6: 59–64), a long time before two lumen catheters were invented. Canaud et al.(Canaud B, Béraud J J, Joyeux H, Mion C: Internal jugular vein cannulation using 2 silicone rubber catheters: A new, simple and safe long-term access for extracorporeal treatment. Nephron 1986; 43: 133–138. Canaud B, Béraud J J, Joyeux H, Mion C: Internal jugular vein cannulation with two silicone rubber catheters: a new and safe temporary vascular access for hemodialysis: Thirty months' experience. Artif Organs 1986; 10: 397–403.) decided to continue the method of Erben et al. using two single-lumen catheters, but they changed material from polyethylene to silicone rubber and used jugular instead of subclavian vein insertion site. The catheters with inner/outer diameters of 2.0/3.2 mm had 6 side holes on the 5 distal centimeters. The catheters were exteriorized by reversed tunneling (from the cervical incision to the skin exit), and extension-tubing adapters were attached to the catheters after their externalization. The catheters were not provided with cuffs.

An important advantage of single catheters is its smaller entrance into the vein and smaller exit site. With the smaller entrance it is more likely to be able to cannulate the vessel repeatedly. The smaller exit is less prone to infections; however, infections were the most common complications of long-term jugular vein catheters (Canaud B. Leray H. Béraud J J. Mion C. Acces vasculaire temporaire: du peripherique au central, du temporaire au permanent. [Temporary vascular access: from peripheral to central, from temporary to permanent]. Nephrologie. 1994; 15: 53_9.). It is worth stressing that these catheters were not provided with cuffs.

Single lumen catheters for single needle dialysis were developed in the late 1980's. A regular, Tenckhoff peritoneal dialysis catheter was used by Liggett et al. (Liggett R A, Kearney M M: Tenckhoff catheter as a primary hemodialysis vascular access. Dialysis & Transplantation,1988; 17: 522–524, 546.) Thrombotic complications of this catheter were frequent as an anticoagulant was leached out of the tip through side holes. A single, silicone rubber catheter with fish-mouth tip to prevent sucking against the vessel wall was developed by Bionic Company (Friedrichsdorf, Germany) and the results with this catheter were reported by Demers et al. (Demers H G, Siebold G, Schielke D J, Mueller W, Niemeyer R, Hoeffler D: Soft right atrial catheter for temporary or permanent vascular access. Dialysis & Transplantation, 1989; 18: 130–139.) The catheter had a single polyester cuff as a barrier to periluminal bacterial penetration, and no side holes at the tip to avoid sucking of the intima and/or leaching out of anticoagulant.

Tesio et al. (Tesio F. De Baz H. Panarello G. Calianno G. Quaia P. Raimondi A. Schinella D. Double catheterization of the internal jugular vein for hemodialysis: indications, techniques, and clinical results. Artif Organs. 1994; 18 :301_4.) used catheters very similar to those of Canaud. These were silicone rubber catheters with internal/external diameters of 2.0/3.2 mm and provided with 6 side holes on the 4 distal cm. Unlike Canaud catheters, Tesio catheters were provided with a 1 cm olive-like device to better fix the cannula in the tunnel. A recent model of Tesio catheter is provided with a small cuff (2 mm wide) located on the olive-shape device. Tesio et al. (Tesio F, De Baz H, Panarello G. Successful Long-term Central Venous Access. Home Hemo Int. 1998; 2: 38–40) describe lower infection rates than that reported by Canaud et al.

Hybrid of Single and Double Lumen Catheter

A hybrid of single and dual lumen catheters, the Ash Split Cath was recently developed by Ash and his colleagues. The intravenous segment is composed of two separate D-shaped lumens, which have multiholed cylindrical tips (Mankus R A. Ash S R. Sutton J M: Comparison of blood flow rates and hydraulic resistance between the Mahurkar catheter, the Tesio twin catheter, and the Ash Split Cath. ASAIO Journal. 1998; 44: M532–4). The transcutaneous portion is a 14 French cylindrically shaped catheter with D-shaped lumens and a polyester cuff. The cylindrical transcutaneous part extends externally and connects through a hub with two transparent lumens attached to Luer lock Whereas the extravascular part and the entrance to the vessel is similar in shape and function to dual lumen catheters, the intravascular part is similar to single lumen catheters. The catheter is inserted with a single vein puncture. Two lumens in the vessel may have advantage over dual lumen by being more flexible.

Hybrids of Subcutaneous and Percutaneous Devices

Two new devices that are hybrids of percutaneous and subcutaneous devices were developed by Biolink Corporation (Middleboro, Mass.) and VascA (Topsfield, Mass.). The first device (Dialock™ Hemodialysis Access System) consists of a port-like valve, implanted subcutaneously below the clavicle, which is connected to two single lumen catheters implanted into the right atrium (Canaud B, My H, Morena M, Lamy-Lacavalerie B, Leray-Moragues H, Bosc J Y, Flavier J L, Chomel P Y, Polaschegg H D, Prosl F R, Megerman J. Dialock: a new vascular access device for extracorporeal renal replacement therapy. Preliminary clinical results. Nephrol Dial Transplant 1999; 14(3):692–8). For each hemodialysis the port is accessed with needle-cannulas, one for inflow, the other for outflow. After dialysis the cannulas are removed and the whole device remains subcutaneously. The second device (LifeSite® Hemodialysis Access System) consists of two subcutaneous valves with an internal pinch clamp that is actuated with a standard 14-gauge dialysis needle, each connected to a single lumen cannula placed in the central venous circulation for hemodialysis. One valve with attached cannula is for blood inflow and the other is for blood outflow (Beathard G A, Posen G A Initial clinical results with the LifeSite® hemodialysis access system. Kidney Int. 2000 Nov;58(5):2221–7). The devices share the advantages and disadvantages of both, subcutaneous and percutaneous blood accesses for hemodialysis.

Complications of Intravenous Catheters

There are two major complications of intravenous catheters: infection and thrombosis. Both are at least partly related to the catheter design.

Infections

There may be exit site/tunnel infection, sepsis, and septic thrombophlebitis.

Measures Preventing Infections

Infection rates may be decreased by catheter design, implantation technique and postimplantation care. Here I will concentrate on catheter features decreasing complications.

Material

Silicone rubber is a preferred material, because of its softness and hydrophobic (water repellant) properties.

Tunnel Length

The length of the tunnel is dependent on the catheter length outside of the vein. The longer the tunnel the less likely it is for the microorganism to penetrate into the blood stream, but in a randomized prospective study, tunneling alone of uncuffed catheters was not found to decrease sepsis rates (von Meyenfeldt M M. Stapert J. de Jong P C. Soeters P B. Wesdorp R I. Greep J M. TPN catheter sepsis: lack of effect of subcutaneous tunneling of PVC catheters on sepsis rate. Jpen: J Parenter Enteral Nutr 1980; 4:514–7). On the other hand the tunnel cannot be too long, so that the exit would not be too low on the chest.

Cuffs

The cuff constitutes a significant barrier for periluminal bacterial penetration and the infection rates with the cuffed catheters are markedly lower than that with uncuffed catheters. There is no question that catheters without cuffs, both intravenous and peritoneal, are associated with very high infection rates and are not suitable for chronic use. Catheter related sepsis was found to be more than ten times higher with uncuffed catheters as compared to cuffed catheters in pediatric population (Rovner M S, Brouhard B H, Cunningham J, Firor H: Comparison of cuffed vs. uncuffed catheters for extracorporeal therapy in pediatric patients. Dialysis & Transplantation 1992; 21: 513–522) Although there are no data on the relationship between the number of cuffs and periluminal infection rates with intravenous catheter, such data exist for peritoneal catheters. A recent publication of the United States Renal Data System reported that compared to double-cuff catheter the risk of peritonitis was 16 and 31% higher for single deep-cuff and single superficial-cuff catheters respectively. (U. S. Renal Data System, USRDS 1992 Annual Data Report, VI. Catheter-Related Factors and Peritonitis Risk in CAPD Patients. Am J Kidney Dis 1992; 5 (Suppl 2): 48–54). Our own study found that the peritonitis rates were lower with triple cuffed catheters compared to the double cuffed catheters (Twardowski Z J, Prowant B F, Nichols W K, Nolph K D, Khanna R: Six-year experience with swan neck catheter. Perit Dial Int 1992; 12:384–389). Exit site infections were also found to be lower with cuffed catheters. Rovner et al. (Rovner M S, Brouhard B H, Cunningham J, Firor H: Comparison of cuffed vs. uncuffed catheters for extracorporeal therapy in pediatric patients. Dial Transplant 1992; 21: 513–522) reported an exit infection rate of 1.26/1000 days, with cuffed catheters compared with a rate of 4.85/1000 days with uncuffed catheters. The reason for higher infection rates with the absence of a cuff is poor immobilization of the catheter that permits catheter movement outside the sinus where it collects contaminants and transfers them deep into the sinus after retraction. Also, catheter movement to and fro in the subcutaneous tunnel causes microtraumas predisposing further to infections.

Lumen Lock

Between hemodialysis sessions, it is customary to lock catheter lumens with anticoagulant to prevent clot formation. Four anticoagulants have been used: heparin, urokinase, tissue plasminogen activator, and sodium citrate. Recently the locking solution has been provided also with antibacterial properties. For this purpose an anticoagulant has been mixed with the antibiotic (Boorgu R, Dubrow A J, Levin N W, My H, Canaud B J, Lentino J R, Wentworth D W, Hatch D A, Megerman J, Prosl F R, Gandhi V C, Ing T S. Adjunctive antibiotic/anticoagulant lock therapy in the treatment of bacteremia associated with the use of a subcutaneously implanted hemodialysis access device. ASAIO J. 2000;46(6):767–70.) No incompatibility was found in tests in vitro if heparin in final concentration of 5,000 U/mL was mixed with vancomycin, ceftazidime, cefazolin, or gentamicin (Vercaigne L M, Sitar D S, Penner S B, Bernstein K, Wang G Q, Burczynski F J. Antibiotic-heparin lock: in vitro antibiotic stability combined with heparin in a central venous catheter. Pharmacotherapy 2000;20(4):394–9.) If this method is used concomitantly with systemic antibiotics for treatment of catheter related bacteremia, the method gives positive results without catheter removal in the majority of cases (Capdevila J A. Catheter-related infection: an update on diagnosis, treatment, and prevention. Int J Infect Dis. 2(4):230–6, 1998. —Sodemann K, Lubrich-Birkner I, Berger O, Baumert J, Feldmer B, von Hodenberg E. Gentamicin/sodium-citrate mixture as antibiotic-lock technique for salvage and prevention of catheter-related infections—A four year trial (abstract). *J Am Soc Nephrol* 8:173A, 1997.

Thrombosis

As early as in the mid $19^{th}$ century, Rudolf Virchow postulated that three factors predispose to phlebothrombosis (clot formation in the vein): hypercoagulable state, vein wall damage, and blood stasis. These three factors are still judged to be the most important, and have to be considered in planning preventive measures. With a foreign body in the blood vessel, an additional factor becomes important: the material from which this foreign body is made.

Measures Preventing Thrombosis

Thrombosis probably cannot be completely eliminated, but its incidence may be reduced by catheter design and appropriate anticoagulation. Only catheter design features decreasing thrombosis rates will be discussed here. These are: material, catheter shape and size, tip configuration, and number of lumens.

Material

Thrombogenicity of material is crucial in the speed of thrombus formation. Due to high thrombogenicity, prolonged catheterization was impossible with glass, polyethylene and polyvinyl cannulae. Polyurethane is claimed to be less thrombogenic than tetrafluoroethylene. In animal studies, silicone rubber catheters showed the lowest thrombogenicity compared to catheters made of other materials (Welch G W, McKell D W, Silverstein P, Walker H L: The role of catheter composition in the development of thrombophlebitis. Surg Gynecol Obstet 1974; 138: 421–442). Silicone rubber is a preferred material to prevent catheter-related thrombosis.

Insertion Site

The repeated damage to the intima seems to be crucial in thrombosis of cannulated veins. A strong argument for this mechanism is more frequent and massive thrombosis seen with left sided cannulation where the vein path is more tortuous (Ratcliffe P J, Oliver D O: Massive thrombosis around subclavian cannulas used for haemodialysis (Letter). Lancet 1982; 1: 1472–1473). In the series of Hoshal et al. (Hoshal V L Jr, Ause R G, Hoskins P A: Fibrin sleeve formation on indwelling subclavian central venous catheters. Arch Surg 1971; 102: 353–358) mural thrombi usually formed at the points where the catheter pressed on the vessel wall, particularly where the tip touched on the intima. In choosing the insertion site these factors should be borne in mind. The jugular route, particularly on the right side, is advantageous since the course of catheter to the right atrium is almost a straight line, minimizing trauma to the intima. The path from the left jugular vein is more tortuous. Subclavian veins are least favorable because of tortuous course, particularly on the left side. Besides, the narrow space between the first rib and the clavicle, where the subclavian vein passes, predisposes to vein wall trauma when movement of the upper extremities squeezes the catheter. Cimochowski et al (Cimochowski G E, Worley E, Rutherford W E, Sartain J, Blondin J, Harter H: Superiority of the internal jugular over the subclavian access for temporary dialysis. Nephron, 1990; 54: 154–161) stressed that vein stenosis is least likely if the stiff catheter is inserted through the right jugular vein. Schillinger et al. (Schillinger F, Schillinger D, Montagnac R, Milcent T: Post catheterisation vein stenosis inhaemodialysis: Comparative angiographic study of 50 subclavian and 50 internal jugular accesses. Nephrol Dial Transplant, 1991; 6: 722–724) evaluated phlebographically the rate of stenosis of the subclavian and/or brachiocephalic vein in cases cannulated previously through the subclavian route or through the jugular route. They found a stenosis in 42% of the subclavian group and in 10% of the jugular group. The right side was cannulated in 58% of cases in the subclavian group and 78% in the jugular group. The rate of stenosis on the left side was higher, particularly in the jugular group (7.7% on the right and 18.2% on the left). It is worth stressing that the authors described the complications with use of stiff catheters.

Side Holes at the Distal End

All catheters for acute hemodialysis are provided with side holes at the distal end. This is supposed to prolong catheter life, assuming that even if the distal bore is occluded by a clot, a few side holes may remain opened providing sufficient blood flow. Most catheters for chronic dialysis, both single and dual lumen, are also provided with side holes. There are no data in support of the notion that side holes prolong the life of chronic catheters. In my opinion the opposite may be true. Firstly, many times, while removing chronic catheters, either electively or because of catheter obstruction, a clot is found attached to the tip of the catheter and anchored in the side hole of the inflow lumen. Such a clot is difficult to remove or dissolve while in situ. Secondly, intraluminal clot is usually easily removed or dissolved (Twardowski Z J: High-dose intradialytic urokinase to restore the patency of permanent central vein hemodialysis catheters. AJKD 1998; 31 (5): 841–847). The clot, which is difficult to remove is formed on the outer surface of the catheter and extends to the inside lumen. If so, the holes have no role in extending the life of the catheter. Thirdly, the heparin solution, which is instilled to the catheter lumen at the end of dialysis, may not reach the catheter tip and/or be leached out in the period between dialyses, thus, predisposing to clot formation at the tip of the inflow lumen. Finally, if the inflow bore is occluded and the blood flows through the side holes, it is likely that the vein intima is sucked into the holes, becomes damaged and causes formation of the clot in the vessel lumen. In such a case these holes would not be beneficial for the catheter life, but maybe even precluding the possibility of inserting another catheter into the same vein at a later time. (Twardowski Z J, Moore H L Side holes at the tip of chronic hemodialysis catheters are harmful. Journal of Vascular Access 2001; 2(1): 8–16).

Shape of the Catheter

It is very likely that the major reason of these complications is pressure of the straight catheter on the vein intima at the "pressure points" where venous path takes a rapid turn. This led us to design a so-called "vein shape catheters", which has been patented (U.S. Pat. Nos. 5,209,723; 5,405,320; 5,509,897; 5,569,182; and 5,685,867). The idea of these catheters is to make the shape of the catheter as similar as possible to the shape of vein where the catheter is located; however, it is difficult to choose the catheter with the shape similar to that of the vein.

Size of the Catheter

Companies manufacturing catheters make them in a few sizes. For instance, Kendall Healthcare (Mansfield, Mass.) makes three sizes of PermCath straight catheters: 36 cm, 40 cm, and 45 cm. The length of the catheter is a total length, from the tip to the luer lock end. BARD (Salt Lake City, Utah) makes three sizes of permanently bent catheters: 19 cm, 23 cm, and 27 cm. The length of the catheter is from the tip to the cuff. The catheters of the same type have the same internal diameter, regardless of their length. This practice causes that the shorter catheters have higher blood flow at the same inflow pressure than the longer catheters.

This approach has disadvantage, as longer catheters, inserted in patients with larger body build, should have higher blood flow to achieve a desired efficiency of dialysis. According to the Dialysis Outcome Quality Initiative (DOQI) recommendations, all patients should have delivered Kt/V of 1.2–1.3. (NKF-DOQI clinical practice guidelines for hemodialysis adequacy. National Kidney Foundation. Am J Kidney Dis. 1997; 30(3 Suppl 2):S15–66.) Kt/V is a product of dialyzer clearance multiplied by time of dialysis and divided by volume of distribution of urea or total body water. Total body water is roughly proportional to the body height and weight (Watson P E, Watson I D, Batt R D. Total body water volumes for adult males and females estimated from simple anthropometric measurements. Am J Clin Nutr. 1980;33(1):27–39.) and clearance is proportional to the blood flow within certain limits depending on the dialyzer mass transfer area coefficient. Thus, to satisfy DOQI requirements, longer catheters, inserted into larger patients, should have higher, not lower, blood flow.

Poiseuille's equation predicts that, in circular tubes, at the same pressure difference and catheter length, the laminar flow is proportional to the $4^{th}$ power of the radius. On the other hand, the catheter diameter cannot be too large to fill the vein too tightly as it predisposes to the damage of vein wall, vein thrombosis and stenosis [Dixit A, Ram S, Zaman F, Pervez A, Torres C, Work J. Does the Ash split catheter have a better survival than the Mahurkar catheter? J Am Soc Nephrol 10: abstract A1042, 1999, Davenport A. Central venous catheters for hemodialysis: How to overcome the problems. Hemodial Int 4:78–82, 2000.] The availability of only a few sizes of the catheters create a problem of locating the catheter tip in an appropriate point in patients of different body builds. Most catheters have internal diameter of 2 mm (PermCath—Kendall Healthcare, Opti-flow (BARD), Tesio—MedComp, Harleysville, Pa.) or 2.2 mm (Dialock—Biolink Corporation, LifeSite—VascA) regardless of catheter length.

For the best performance the tip of a central vein catheter for hemodialysis should be located in the right cardiac cavities [Jean G, Chazot C, Vanel T, Charra B, Terrat J C, Calemard E, Laurent G. Central venous catheters for hemodialysis: looking for optimal blood flow. Nephrol Dial Transplant 12(8):1689–91, 1997]. Schwab and Beathard recommend catheter tip localization in the middle of the right atrium, while the patient is supine, so it will move no higher than to the lower superior vena cava while the patient is upright [Schwab S J, Beathard G. The Hemodialysis Catheter Conundrum: Hate Living with Them, But Can't Live Without Them.] (Kidney Int. 1999; 56: 1–17). Both too high and too low positions of the catheter tip are unfavorable. The heart moves down in the upright position and up in the supine position. Because the catheter length is fixed, the catheter moves deeper into the right atrium, while the patient is supine, and closer to the brachial veins, while the patient is upright. Breathing also influences catheter position. During deep inspiration the diaphragm and the heart move down so the catheter tip moves up; during expiration the movements are in opposite directions. Finally, the chest wall subcutaneous tissue moves down when the supine person assumes the erect posture (Schwab S J, Beathard G. ibid) The catheter cuff, which is anchored in this tissue, pulls the catheter tip upward.

If the catheter tip is located high in the superior vena cava it may translocate to one of the brachiocephalic veins where the blood flow is insufficient to secure adequate blood flow through the dialyzer. If the catheter tip is too low it may move to a cusp of the thebesian or eustachian valve, or migrate to the inferior vena cava or to the right ventricle. All this positions are unfavorable for catheter function. The catheter tip in the inferior vena cava gives apparently paradoxical low recirculation values with reversed lines (Twardowski Z J, Nichols W K, Van Stone J C, Haynie J: All currently used measurements of recirculation in blood access by chemical methods are flawed due to intradialytic disequilibrium or recirculation at low flow. Am J Kidney Dis 32 (6): 1046–1058, 1998.) and provides high recirculation values with standard direction of lines. If catheter migrates to the right ventricle, it may become entangled in the papillary muscles and become obstructed (Twardowski Z J: Nichols W K: Opti-flow catheter tip translocation from the right atrium to the right ventricle. Journal of Vascular Access 2001; 2(1): 17–19. Too low position of the catheter tip in the right atrium predisposes to formation of the right atrial thrombus ([Gilon D, Schechter D, Rein A J, Gimmon Z, Or R, Rozenman Y, Slavin S, Gotsman M S, Nagler A. Right atrial thrombi are related to indwelling central venous catheter position: insights into time course and possible mechanism of formation. Am Heart J. 135(3):457–62, 1998. Korones D N, Buzzard C J, Asselin B L, Harris J P. Right atrial thrombi in children with cancer and indwelling catheters. J Pediatr 128(6):841–6, 1996). All these problems require that a catheter length be precisely selected for a patient. I believe that the best compromise between conflicting requirements is to locate the catheter tip in the upper right atrium (URA).

Optimal Lengths and Diameters of Catheters

A study in 31 volunteers of large upper body veins using magnetic resonance imaging showed a great variability in vein dimensions and shapes even in persons with the same body build. (Twardowski, Z J and Seger R M: Dimensions of central venous structures in humans measured in vivo using magnetic resonance imaging: Implications for central vein catheter dimensions *The International Journal of Artificial Organs,* Vol. 25, 2, 2002, pp. 107–123). In this study, the shapes and distances from the insertion sites in jugular and subclavian veins to the right atrium were determined and correlated with the height, acromion-distance, weight, body surface area, and combinations thereof.

The tip of the dual lumen, straight catheters such as VasCath™ (BARD, Salt Lake City, Utah, USA) or Perm- Cath® (Kendall Healthcare, Mansfield, Mass., USA) may be properly positioned, if x-ray is used during catheter implantation. Because straight catheters are prone to kinking after implantation, the manufacturers supplemented these catheters with permanently bent catheters: Opti-Flow™ (BARD, Salt Lake City, Utah) or Swan Neck™ PermCath™ (Kendall Healthcare, Mansfield, Mass.). If these catheters are inserted through an internal jugular vein, the bend is located over the clavicle. Although insertion through the internal jugular vein is preferred, the catheters may be inserted through the subclavian veins. In these cases the bend is located below the clavicle. The length from the bend to the tip is essentially fixed; therefore the catheter length should be selected for the patient. If there is no guidance as to the appropriate length of the bent catheter, the catheter tip maybe located too high or too low. For this purpose, the exact dimensions of the venous system in vivo should be known; otherwise the catheter selection would be based on guessing and the tip may translocate later to the improper position (Twardowski Z J: Nichols, W K: Opti-flow catheter tip translocation from the right atrium to the right ventricle. Ibid.

A perfect position of the tip of the bent catheter could be achieved if magnetic resonance image were performed in a patient before catheter implantation and the precise measurements were performed as described in the methods section of the magnetic resonance imaging study [Twardowski Z J and Seger R M: Dimensions of central venous structures in humans measured in vivo using magnetic resonance imaging: Implications for central vein catheter dimensions—unpublished, manuscript attached]. Another approach would be to implant a catheter basing the selection on guessing and replace for another if the guess was wrong. Both approaches, however, would be costly and impractical. It is much more convenient for the operator to know the optimal choice of the catheter length before the procedure. The ranges of vein dimensions with the same body size are considerable. Fortunately the acceptable position of the catheter tip ranges from the middle of the right atrium to the lower superior vena cava and the selection of a catheter guided by our study will usually be adequate. The most practical and effective approach to the selection of the appropriate catheter length is to take into account body surface area of the patient.

DESCRIPTION OF THE INVENTION

Accordingly, there is a need to determine for an individual patient a precise optimum catheter length and inner diameter that would best suit the patient as a permanent, implantable catheter. When optimum catheter dimensions are provided to the patient, the tip of the catheter will more reliably stay in the upper right atrium, so that the catheter will function better. Also, thrombosis rates can be decreased, and the overall catheter survival increased, by the selection and provision of a properly sized catheter for the patient. Surprisingly, the desired length, and consequently the desired internal diameter of catheters, strongly correlate with the body surface area of the patient. In other words, a short, stocky patient and a tall, thin patient may have similar body surface areas, and, surprisingly, may have optimum catheter lengths for a particular implantation that are similar.

In accordance with this invention, a method is provided for selecting and implanting a permanent, venous catheter into a patient for use in chronic extracorporeal blood treatment procedures. The steps of the method comprise:

1. Determining the body surface area (BSA) of the patient. This is a known medical procedure, and it maybe determined in customary manner, to preferably obtain the body surface area in square meters.

2. One then selects a permanent venous catheter having an actual length from the catheter distal tip to its integral, proximal end which is within 10% of a desired length, typically in cm, as indicated in Table I below for the body surface area (BSA) of the particular patient, and a particular vein through which the catheter is to extend: namely the right internal jugular vein (RIJV); the right subclavian vein (RSCV); the left internal jugular vein (LIJV); or the left subclavian vein (LSCV):

TABLE I

| BSA $m^2$ | DESIRED LENGTH (cm.) | | | |
|---|---|---|---|---|
| | RIJV cm | RSCV cm | LIJV cm | LSCV cm |
| 1.20 | 22.6 | 23.5 | 25.1 | 26.6 |
| 1.25 | 23.0 | 24.0 | 25.6 | 27.1 |
| 1.30 | 23.4 | 24.4 | 26.0 | 27.6 |
| 1.35 | 23.8 | 24.8 | 26.5 | 28.1 |
| 1.40 | 24.2 | 25.3 | 26.9 | 28.5 |
| 1.45 | 24.6 | 25.7 | 27.4 | 29.0 |
| 1.50 | 25.0 | 26.1 | 27.8 | 29.5 |
| 1.55 | 25.4 | 26.5 | 28.3 | 30.0 |
| 1.60 | 25.8 | 27.0 | 28.7 | 30.4 |
| 1.65 | 26.2 | 27.4 | 29.1 | 30.9 |
| 1.70 | 26.6 | 27.8 | 29.6 | 31.4 |
| 1.75 | 27.0 | 28.3 | 30.0 | 31.9 |
| 1.80 | 27.4 | 28.7 | 30.5 | 32.3 |
| 1.85 | 27.8 | 29.1 | 30.9 | 32.8 |
| 1.90 | 28.2 | 29.5 | 31.4 | 33.3 |
| 1.95 | 28.6 | 30.0 | 31.8 | 33.8 |
| 2.00 | 28.9 | 30.4 | 32.3 | 34.3 |
| 2.10 | 29.7 | 31.3 | 33.2 | 35.2 |
| 2.20 | 30.5 | 32.1 | 34.1 | 36.2 |
| 2.30 | 31.3 | 33.0 | 34.9 | 37.1 |
| 2.45 | 32.5 | 34.3 | 36.3 | 38.5 |
| 2.60 | 33.7 | 35.6 | 37.6 | 40.0 |
| 2.75 | 34.9 | 36.8 | 39.0 | 41.4 |

3. As a final step, the venous catheter is implanted in the desired venous system of the patient, with the distal tip of the catheter being in or adjacent to the upper right atrium of the heart.

Alternatively, a similar method for selecting and implanting a permanent venous catheter into the patient may comprise the similar steps of: (1) determining the body surface area (BSA) of the patient; (2) selecting a permanent venous catheter having an actual length from the catheter distal tip to the point on the catheter where it is to penetrate the wall of the desired vein into which it is to be implanted, said actual length of the catheter being within 10% of a desired length as indicated in Table 2 below for the body surface area (BSA) of the particular patient and the particular vein through which the catheter is to extend (RJIV; RSCV; LIJV; or LSCV.)

TABLE 2

| BSA $m^2$ | RIJV cm | RSCV cm | LIJV cm | LSCV cm |
|---|---|---|---|---|
| 1.20 | 11.1 | 13.4 | 13.9 | 16.5 |
| 1.25 | 11.2 | 13.5 | 14.1 | 16.7 |
| 1.30 | 11.4 | 13.7 | 14.2 | 16.9 |
| 1.35 | 11.5 | 13.8 | 14.4 | 17.1 |
| 1.40 | 11.7 | 13.9 | 14.6 | 17.3 |
| 1.45 | 11.9 | 14.1 | 14.8 | 17.5 |
| 1.50 | 12.0 | 14.2 | 15.0 | 17.7 |
| 1.55 | 12.2 | 14.4 | 15.1 | 17.9 |
| 1.60 | 12.3 | 14.5 | 15.3 | 18.1 |
| 1.65 | 12.5 | 14.6 | 15.5 | 18.3 |
| 1.70 | 12.6 | 14.8 | 15.7 | 18.5 |

TABLE 2-continued

| BSA m² | RIJV cm | RSCV cm | LIJV cm | LSCV cm |
|---|---|---|---|---|
| 1.75 | 12.8 | 14.9 | 15.9 | 18.7 |
| 1.80 | 12.9 | 15.1 | 16.1 | 18.9 |
| 1.85 | 13.1 | 15.2 | 16.2 | 19.1 |
| 1.90 | 13.2 | 15.3 | 16.4 | 19.3 |
| 1.95 | 13.4 | 15.5 | 16.6 | 19.5 |
| 2.00 | 13.5 | 15.6 | 16.8 | 19.7 |
| 2.10 | 13.8 | 15.9 | 17.1 | 20.1 |
| 2.20 | 14.2 | 16.2 | 17.5 | 20.5 |
| 2.30 | 14.5 | 16.5 | 17.9 | 20.9 |
| 2.45 | 14.9 | 16.9 | 18.4 | 21.5 |
| 2.60 | 15.4 | 17.3 | 19.0 | 22.1 |
| 2.75 | 15.8 | 17.7 | 19.5 | 22.7 |

3. As a third step, one implants the selected venous catheter in the desired venous system of the patient with the distal tip of the catheter being in or adjacent to the upper right atrium of the heart.

As a further optional step, after selecting the desired actual catheter length and the particular vein for implantation, one selects a desired flow rate for the catheter, to obtain a catheter having an actual length within 10% of the desired length and an actual inner diameter within 3% of a desired inner diameter as indicated in Table 3 below, correlated with the actual length.

Desired tubing internal diameter in relation to tubing length at constant flow/pressure relationship.

TABLE 3

| Total Length (cm) | Flow of 150–250 ml/min Internal diam. (cm) | Flow of 250–350 ml/min Internal diam. (cm) | Flow of 350–450 ml/min Internal diam. (cm) | Flow of 450–55 ml/min Internal diam. (cm) |
|---|---|---|---|---|
| 22 | 0.156 | 0.172 | 0.185 | 0.196 |
| 23 | 0.157 | 0.174 | 0.187 | 0.198 |
| 24 | 0.159 | 0.176 | 0.189 | 0.200 |
| 25 | 0.161 | 0.178 | 0.191 | 0.202 |
| 26 | 0.162 | 0.180 | 0.193 | 0.204 |
| 27 | 0.164 | 0.181 | 0.195 | 0.206 |
| 28 | 0.165 | 0.183 | 0.197 | 0.208 |
| 29 | 0.167 | 0.185 | 0.198 | 0.210 |
| 30 | 0.168 | 0.186 | 0.200 | 0.211 |
| 31 | 0.170 | 0.188 | 0.202 | 0.213 |
| 32 | 0.171 | 0.189 | 0.203 | 0.215 |
| 33 | 0.172 | 0.191 | 0.205 | 0.217 |
| 34 | 0.174 | 0.192 | 0.206 | 0.218 |
| 35 | 0.175 | 0.193 | 0.208 | 0.220 |
| 36 | 0.176 | 0.195 | 0.209 | 0.221 |
| 37 | 0.177 | 0.196 | 0.211 | 0.223 |
| 38 | 0.178 | 0.197 | 0.212 | 0.224 |
| 39 | 0.180 | 0.199 | 0.214 | 0.226 |
| 40 | 0.181 | 0.200 | 0.215 | 0.227 |
| 41 | 0.182 | 0.201 | 0.216 | 0.229 |
| 42 | 0.183 | 0.202 | 0.218 | 0.230 |

By way of clarification, the term "desired length" is a theoretical, perfect length for the catheter under the selected circumstances. However, in view of practicalities, the actual length of the catheter is of course the length of the actual catheter selected, which is preferably within 10% of the desired length, and preferably within 5% thereof.

If desired, a catheter of known length maybe selected without recourse to body surface area, following which a desired catheter inner diameter maybe selected correlating with the actual length, depending upon the expected flow rate through the catheter, in accordance with this invention.

Thus, a properly sized permanent, venous catheter may be selected and used for a particular patient and a particular site of implantation by a system which correlates with the body surface area (BSA) of the patient to obtain an optimum catheter length, either a length that extends from the catheter distal tip to its integral proximal end or a length of that portion of the catheter which is actually implanted in the particular vein. It should be added that the integral, proximal end of the catheter represents the end of the catheter without any detachable extension tubes or the like, and which integral proximal end of the catheter typically extends out through the skin of the patient after implantation by a short distance, for example, two to six cm. Then, as disclosed in my previous U.S. Pat. No. 5,405,320 and others, an extension tube may be attached to the catheter proximal end, so that the regular and frequent catheter connection and disconnection to hemodialysis sets can be made against the extension tube. Then, when the extension tube wears out, it maybe replaced, so that wear on the actual catheter itself is minimized.

With a properly selected catheter length for the particular patient and the chosen site of venous implantation, one may select a desired flow rate through the catheter, and from that, one may select a desired inner diameter dependent upon the actual length of the catheter, which inner diameter optimally balances the desired flow rate through the catheter with a minimum catheter diameter, to minimize interference with blood flow in the vein by the implanted catheter, while providing adequate, desired blood flow through the catheter. In particular, longer catheters may, with the inner diameters proposed herein, have equal and proper blood flow rates at normal pressures of hemodialysis when compared with shorter catheters.

In accordance with this invention, to select a catheter for one of the permanent venous implantations as illustrated in FIGS. 1 and 2, one may first determine the body surface area of the patient, for example by the well-known method of DuBois et al.; Arch. Int. Med. 17: 863–871 (1916).

From the body surface area and the desired vein in which implantation is to be made (RIJV, RSCV, LIJV, or LSCV), one can determine the desired length in cm. in accordance with Table 1 or Table 2, depending upon which length of the catheter is desired to be used for catheter selection. Then, an optimum tubing inner diameter for the catheter may be determined from the length of the catheter determined in the previous step in accordance with Table 3. Based on this, an actual catheter may be selected which is within 10% of the desired length and 3% of the desired inner diameter. Such a catheter may be implanted, and will exhibit improvements with that particular patient over catheters of differing dimensions. These improvements may comprise a decreased probability of atrial thrombosis, coupled with improved probability of appropriate blood flow, optimization of blood flow, less vein thrombosis and stenosis, increased probability of adequate dialysis, improved catheter survival, and decreased patient morbidity.

If desired, one may correlate a catheter's length to its desired inner diameter without regard to the body surface area of the patient. This in itself can provide significant advantages of flow optimization.

Straight line interpolation from the various Tables may be used when needed.

Advantages and Disadvantages of Dual Lumen Catheters

The main advantage of dual lumen catheters is convenience of insertion. Instead of two punctures only one puncture is required. This decreases the insertion time considerably and may decrease complication rates related to the insertion procedure itself. This feature was very important when stiff catheters for acute dialysis were used because the catheter was inserted for only a few days. For chronic dialysis this feature is less relevant, because the catheters are used for several months or years and decrease of thrombotic and infectious complications takes precedence over convenience and complication rates during insertion. Besides, complication rates during insertion of soft catheters are very low.

The main disadvantage of dual catheters is their large diameter. The larger diameter the more damage to the vessel wall and the higher exit-site infection rates. As mentioned above, compared to single lumen catheter, dual lumen catheter is stiffer at the same durameter (hardness) of material. Consequently the damage to the pressure points (see above) is more pronounced.

Disadvantages of Single Lumen (Canaud and Tesio) Catheters

The major advantages of single lumen catheters are their smaller diameter and better flexibility. This decreases damage to the vessel wall, vein intima, and decreases exit site infection rates. If both catheters are implanted into the same vein, then the total diameter of two catheters is bigger than that of dual lumen catheter. The advantage of smaller lumen shows only if the catheters are implanted through two veins, e.g., jugulars on each side or jugular and subclavian on the same side. It is worth stressing that the diameter of brachiocephalic veins is bigger than diameter of either jugular or subclavian veins (Table 2).

In this invention, the catheters for long-term hemodialysis access are intended to be inserted into the upper right atrium through one of the following veins:

1. Right internal or external jugular vein
2. Left internal or external jugular vein
3. Right subclavian vein
4. Left subclavian vein The intravenous catheter of this invention comprises a flexible catheter body, which may be made of medical grade polyurethane, silicone rubber or equivalent material. The catheter may have either single lumen or two lumens. The distal end portion defines flow tubing for blood communication between the lumen and the vein. The tip of the catheter may be provided with side hole(s), although preferably the holes should be absent. The proximal end portion defines a flow tubing for communication with the extension set, which may be coupled with any blood withdrawal and/or intravenous fluid delivery system, such as hemodialyzer, hemofilter, plasmapheresis apparatus, etc. The catheter is preferably provided also with one or two cuffs (subcutaneous or external and deep or internal), which are the bands of fabric affixed to the catheter body (tubing) for fibrous tissue ingrowth in the catheter tunnel.

Implantation of the catheter may be performed either surgically in an operating room or in a procedure room under sterile conditions. After anesthetizing the skin over the intended insertion site, a small, 1–3 cm skin incision is made and dissected bluntly closer toward the vein. The Seldinger method of catheter insertion, already described above, is a preferred method of catheter insertion into the vein. The catheter length and diameter is chosen according to the body size as shown in the table below. A proximal end portion is then used as a gauge to mark the positions of the external cuff and the exit. Using a small hemostat or other suitable instrument a tunnel is made from the incision to the level where the external cuff will lodge. A trocar with the external diameter identical to the catheter tubing is attached to the external end of the catheter, passed through the exit site and the catheter is pulled through the exit. An extension set is then attached to the catheter, and the catheter is covered with immobilizing dressing. Because the external cuff is bigger then the last portion of the subcutaneous tunnel, the catheter cannot dislodge outside, thus no anchoring suture is needed at the exit site.

Relative to the human body after the implantation the catheter consists of three segments: 1) intravenous catheter segment is the part of the catheter located intravenously; the length of this part in relation to body surface area is given in table 2; 2) intramural catheter segment is the part of the catheter contained within the tunnel; and 3) external catheter segment is the part of the catheter outside the skin exit. The catheter tunnel is the passageway through the thoracic wall within which the catheter is contained. Internal tunnel exit is the inlet of the tunnel into the vein. Skin exit is the skin outlet of the tunnel. Subcutaneous or superficial or outer or external cuff is located close (1–3 cm) to the skin exit. The inner or deep cuff is located 2–6 cm from the external cuff, closer to the vein. The part of the tunnel between the skin exit and the outer cuff constitutes the sinus tract.

The catheter may be made radiopaque by addition of barium sulfate or other suitable material into the catheter body. This will facilitate visualization of the catheter on an X-ray.

Subcutaneous cuffs provide both bacteriological barrier against tunnel infection and anchoring means of the intramural and external catheter segments minimizing the movement of the catheter into and out of the tunnel. As mentioned above, such a movement predisposes to contamination of the tubing with introduction of contaminants into the sinus tract after its retraction. Downward directed skin exit for the catheter further decreases chances of sinus tract contamination with the down flowing sweat and bacteria laden water. Also, downward directed exit facilitates pus drainage should infection occur.

The external segment of the catheter typically protrudes about 2 to 6 cm., typically about three cm. out of the skin and may be attached to an extension set consisting of a connector having a flexible extension tube, approximately 8 centimeters in length and equipped with a female luer lock adapter and sealing cap. The extension set is attached to the catheter body after the catheter is inserted into the vein and the subcutaneous tunnel is created. If the extension set is attached to the catheter body before implantation, then the standard tunneling method must be used. During the connection procedure for fluid delivery and/or blood egress the extension tube is clamped, the cap is removed and an appropriate male A male luer adapter is coupled with the female luer lock adapter of the extension tube. After prolonged use, the extension tube may be damaged to the extent that it has to be replaced. The connector facilitates the replacement without the necessity of the catheter removal.

One single lumen catheter may be used for drug delivery, parenteral nutrition, and blood withdrawal for repeated laboratory tests. Although one catheter may be used for blood purification procedure (hemodialysis, plasmapheresis, hemofiltration, etc) two catheters are preferred, one for inflow and one for outflow. If two catheters are inserted, the tips of the catheters should preferentially be a few centimeters apart with the outflow closer to the right atrium. Two catheters may be inserted through the same vein or through two veins. From the convenience point of view it is better to insert both catheters through the same vein; however, to avoid damage of vein wall, vein thrombosis and stenosis the vein should not be filled too tightly, so it is better to insert the catheters through two veins. Any combination of insertion sites may be used, e.g., one catheter inserted through the right internal jugular vein and the other through the left subclavian vein. As mentioned above, dual lumen catheters are more convenient from the insertion point of view. The Tables above provide optimum lumen lengths for dual lumen catheters in the same manner as single lumen catheters.

DETAILED DESCRIPTION OF THE INVENTION

Figure 1:
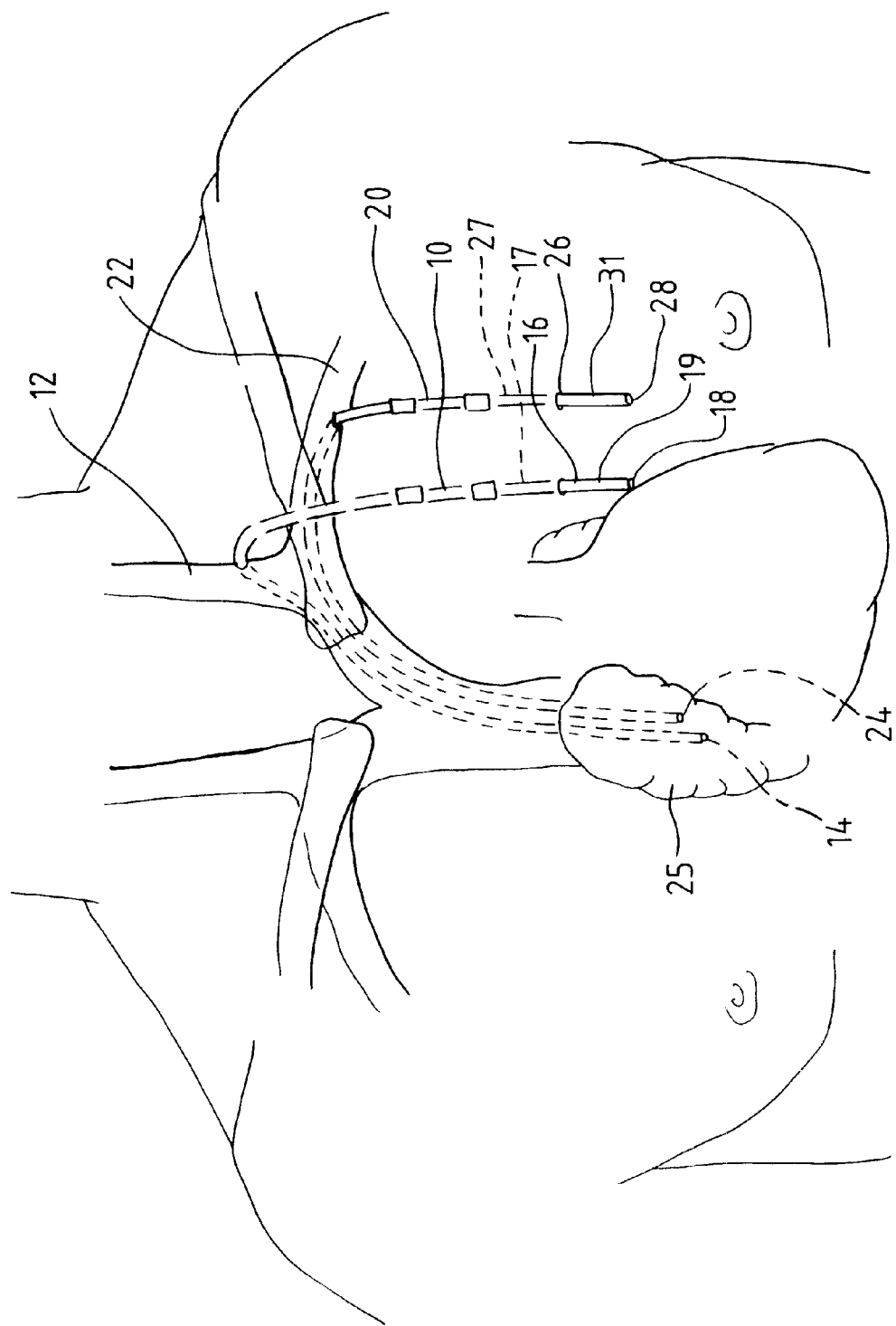
FIG. 1 is a view of two single lumen catheters implanted in a patient through the left subclavian vein and left jugular vein.

As shown in FIG. 1, the catheter 10 enters the left internal jugular vein 12, and its tip 14 is located in the right upper atrium 25. The exit 16 from tissue tunnel 17 is on the chest and the external part,3 cm long, is protruding out of the skin. A known luer lock extension will generally be attached to the proximal catheter end 19 and the lumen 18.

Catheter 20 enters the left subclavian vein 22, and its tip 24 is also located in the upper right atrium 25. The exit 26 from tissue tunnel 27 is on the chest, and the proximal, external catheter part 31 protrudes about 3 cm out of the exit 26. The external bore 28 of the catheter may be attached to another luer lock extension. The catheter tip of the subclavian catheter 24 is preferably slightly higher in this embodiment than the other catheter tip 14, as it is intended for inflow.

Figure 2:
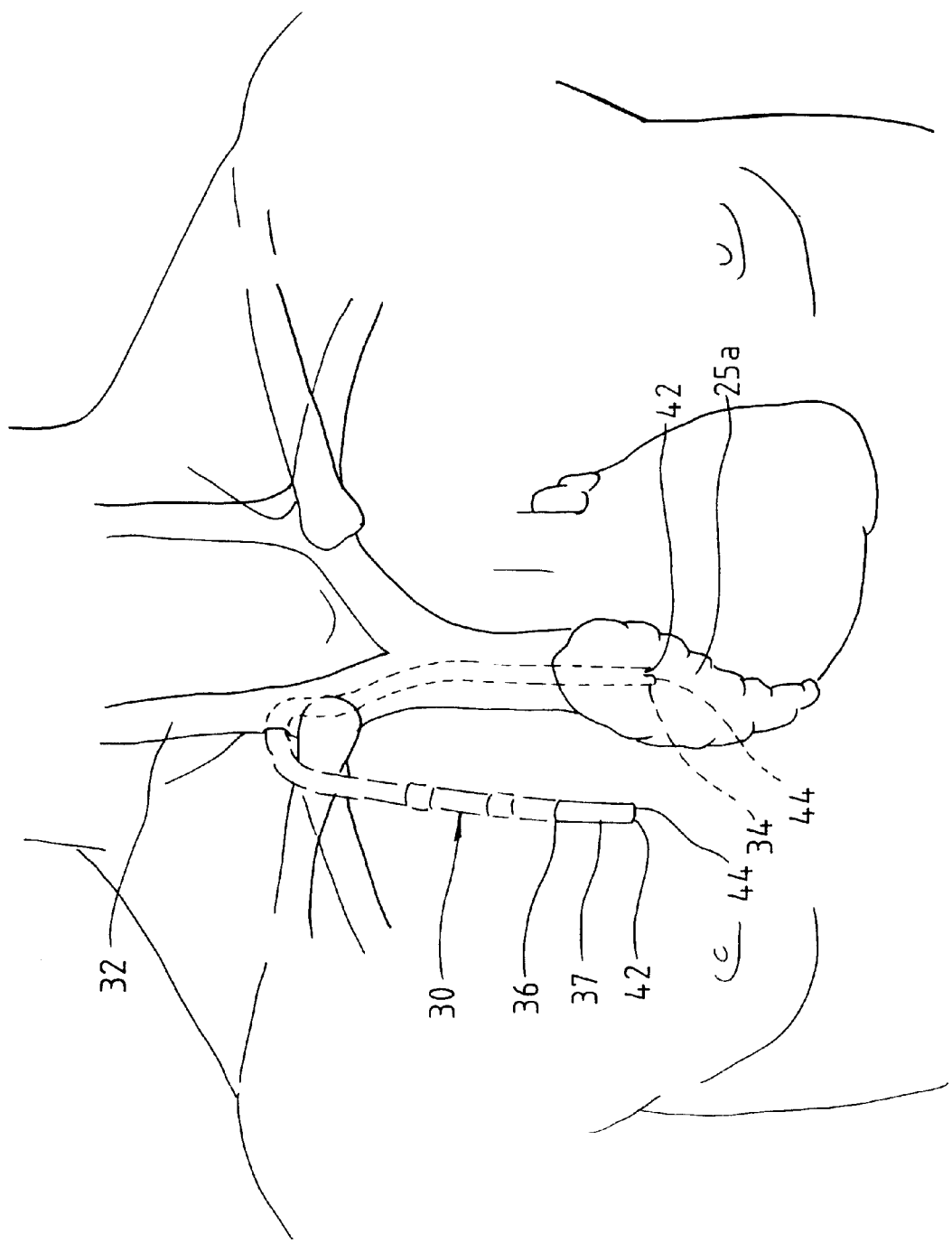
FIG. 2 is a view of the dual lumen catheter implanted in a patient through the right jugular vein.

The dual lumen catheter 30 in FIG. 2 enters the jugular vein 32 and its tip 34 is located in the right upper atrium 25a. The end of the inflow lumen 42 maybe located about 0.5 cm. higher than the outflow lumen 44, particularly at flow rates under 300 ml/min. At higher flow rates, the catheter end may preferably be flush if desired. The external catheter end part 37 protrudes about 3 cm out of the tunnel exit 36. The external ends of bores 42, 44 of the catheter may be connected to an extension tube.

Before implantation, the catheters are selected in a manner dependent on the patient body surface area and the implantation site. The outflow lumen bore 44 may end lower in the right atrium 25a than the inflow bore 42.

To cover the whole range of body sizes in adult population, at least nine lengths of the catheters should preferably be available. Catheter tips of single lumen catheters maybe located at the same level in the upper right atrium. Catheter diameters may be adjusted to the catheter lengths as previously described so as to provide standardized blood flows.

The above has been offered for illustrative purposes only and is not intended to limit the scope of the invention of this application, which is as defined in the claims below.

That which is claimed:

1. The method of selecting and implanting a permanent venous catheter into a patient for use in chronic extracorporeal blood treatment procedures, which comprises:
    determining the Body Surface Area (BSA) of the patient;
    selecting a permanent venous catheter having an actual length from the catheter distal tip to its integral, proximal end which is within ten percent of a desired length in cm. as indicated in the Table below for the Body Surface Area of the particular patient and a particular vein through which the catheter is to extend (RIJV; RSCV; LIJV; or LSCV):

| BSA m² | DESIRED LENGTH (cm.) | | | |
|---|---|---|---|---|
| | RIJV cm | RSCV cm | LIJV cm | LSCV cm |
| 1.20 | 22.6 | 23.5 | 25.1 | 26.6 |
| 1.25 | 23.0 | 24.0 | 25.6 | 27.1 |
| 1.30 | 23.4 | 24.4 | 26.0 | 27.6 |
| 1.35 | 23.8 | 24.8 | 26.5 | 28.1 |
| 1.40 | 24.2 | 25.3 | 26.9 | 28.5 |
| 1.45 | 24.6 | 25.7 | 27.4 | 29.0 |
| 1.50 | 25.0 | 26.1 | 27.8 | 29.5 |
| 1.55 | 25.4 | 26.5 | 28.3 | 30.0 |
| 1.60 | 25.8 | 27.0 | 28.7 | 30.4 |
| 1.65 | 26.2 | 27.4 | 29.1 | 30.9 |
| 1.70 | 26.6 | 27.8 | 29.6 | 31.4 |
| 1.75 | 27.0 | 28.3 | 30.0 | 31.9 |
| 1.80 | 27.4 | 28.7 | 30.5 | 32.3 |
| 1.85 | 27.8 | 29.1 | 30.9 | 32.8 |
| 1.90 | 28.2 | 29.5 | 31.4 | 33.3 |
| 1.95 | 28.6 | 30.0 | 31.8 | 33.8 |
| 2.00 | 28.9 | 30.4 | 32.3 | 34.3 |
| 2.10 | 29.7 | 31.3 | 33.2 | 35.2 |
| 2.20 | 30.5 | 32.1 | 34.1 | 36.2 |
| 2.30 | 31.3 | 33.0 | 34.9 | 37.1 |
| 2.45 | 32.5 | 34.3 | 36.3 | 38.5 |
| 2.60 | 33.7 | 35.6 | 37.6 | 40.0 |
| 2.75 | 34.9 | 36.8 | 39.0 | 41.4 | and implanting the venous catheter in the venous system of the patient with the distal tip of the catheter being in or adjacent to the upper right atrium of the heart.

2. The method of claim 1, further including the step of:
    after selecting said actual length for a catheter within 10 percent of said desired length and said particular vein, selecting a desired flow rate of 150 to 250 ml. per minute; and obtaining a catheter having said actual length and an actual inner diameter within 3 percent of a desired inner diameter indicated in the Table below for the actual length:

| TUBING INTERNAL DIAMETER IN RELATION TUBING LENGTH | |
|---|---|
| Actual Length (cm.) | Inner Diameter (cm.) |
| 22 | 0.156 |
| 23 | 0.157 |
| 24 | 0.159 |
| 25 | 0.161 |
| 26 | 0.162 |
| 27 | 0.164 |
| 28 | 0.165 |
| 29 | 0.167 |
| 30 | 0.168 |
| 31 | 0.170 |
| 32 | 0.171 |
| 33 | 0.172 |
| 34 | 0.174 |
| 35 | 0.175 |
| 36 | 0.176 |
| 37 | 0.177 |
| 38 | 0.178 |
| 39 | 0.180 |
| 40 | 0.181 |
| 41 | 0.182 |
| 42 | 0.183 |

3. The method of claim 2, in which said actual inner diameter is within 2 percent of the desired inner diameter.

4. The method of claim 1, further including the step of: after selecting said actual length for a catheter within 10 percent of said desired length and said particular vein, selecting a desired flow rate of 250 to 350 ml. per minute; and obtaining a catheter having said actual length and an actual inner diameter within 3 percent of a desired inner diameter indicated in the Table below for the actual length:

| Actual Length (cm.) | Inner Diameter (cm.) |
| --- | --- |
| 22 | 0.172 |
| 23 | 0.174 |
| 24 | 0.176 |
| 25 | 0.178 |
| 26 | 0.180 |
| 27 | 0.181 |
| 28 | 0.183 |
| 29 | 0.185 |
| 30 | 0.186 |
| 31 | 0.188 |
| 32 | 0.189 |
| 33 | 0.191 |
| 34 | 0.192 |
| 35 | 0.193 |
| 36 | 0.195 |
| 37 | 0.196 |
| 38 | 0.197 |
| 39 | 0.199 |
| 40 | 0.200 |
| 41 | 0.201 |
| 42 | 0.202 |

5. The method of claim 4 in which said actual inner diameter is within 2 percent of the desired inner diameter.

6. The method of claim 1, further including the step of: after selecting said actual length for a catheter within 10 percent of said desired length and said particular vein, selecting a desired flow rate of 350 to 450 ml. per minute; and obtaining a catheter having said actual length and an actual inner diameter within 3 percent of a desired inner diameter indicated in the Table below for the actual length:

| Actual Length (cm.) | Inner Diameter (cm.) |
| --- | --- |
| 22 | 0.185 |
| 23 | 0.187 |
| 24 | 0.189 |
| 25 | 0.191 |
| 26 | 0.193 |
| 27 | 0.195 |
| 28 | 0.197 |
| 29 | 0.198 |
| 30 | 0.200 |
| 31 | 0.202 |
| 32 | 0.203 |
| 33 | 0.205 |
| 34 | 0.206 |
| 35 | 0.208 |
| 36 | 0.209 |
| 37 | 0.211 |
| 38 | 0.212 |
| 39 | 0.214 |
| 40 | 0.215 |
| 41 | 0.216 |
| 42 | 0.218 |

7. The method of claim 6 in which said actual inner diameter is within 2 percent of the desired inner diameter.

8. The method of claim 1, further including the step of: after selecting said actual length within 10 percent of said desired length and said particular vein, selecting a desired flow rate of 450 to 550 ml. per minute; and obtaining said catheter having an actual inner diameter within 3 percent of the desired inner diameter indicated in the Table below for the actual length:

| Actual Length (cm.) | Inner Diameter (cm.) |
| --- | --- |
| 22 | 0.196 |
| 23 | 0.198 |
| 24 | 0.200 |
| 25 | 0.202 |
| 26 | 0.204 |
| 27 | 0.206 |
| 28 | 0.208 |
| 29 | 0.210 |
| 30 | 0.211 |
| 31 | 0.213 |
| 32 | 0.215 |
| 33 | 0.217 |
| 34 | 0.218 |
| 35 | 0.220 |
| 36 | 0.221 |
| 37 | 0.223 |
| 38 | 0.224 |
| 39 | 0.226 |
| 40 | 0.227 |
| 41 | 0.229 |
| 42 | 0.230 |

9. The method of claim 8 in which said actual inner diameter is within 2 percent of the desired inner diameter.

10. The method of selecting and implanting a permanent venous catheter into a patient for use in chronic extracorporeal blood treatment procedures, which comprises: selecting a desired flow rate of 150 to 250 ml. per minute for a catheter to be implanted in a patient; selecting a permanent venous catheter having an actual length from the catheter distal tip to its integral, proximal end of 22–42 cm., said catheter having a lumen with an actual inner diameter within 3 percent of a desired inner diameter indicated in the Table below for the particular actual length:

| Actual Length (cm.) | Inner Diameter (cm.) |
| --- | --- |
| 22 | 0.156 |
| 23 | 0.157 |
| 24 | 0.159 |
| 25 | 0.161 |
| 26 | 0.162 |
| 27 | 0.164 |
| 28 | 0.165 |
| 29 | 0.167 |
| 30 | 0.168 |
| 31 | 0.170 |
| 32 | 0.171 |
| 33 | 0.172 |
| 34 | 0.174 |
| 35 | 0.175 |
| 36 | 0.176 |
| 37 | 0.177 |
| 38 | 0.178 |
| 39 | 0.180 |
| 40 | 0.181 |
| 41 | 0.182 |
| 42 | 0.183 | and implanting the venous catheter in the venous system of the patient.

11. The method of claim 10 in which said actual inner diameter is within 2 percent of the desired inner diameter.

12. The method of selecting and implanting a permanent venous catheter into a patient for use in chronic extracorporeal blood treatment procedures, which comprises: selecting a desired flow rate of 250 to 350 ml. per minute for a catheter to be implanted in a patient; selecting a permanent venous catheter having an actual length from the catheter distal tip to its integral, proximal end of 22–42 cm., said catheter having a lumen with an actual diameter within 3 percent of a desired inner diameter indicated in the Table below for the particular actual length:

| Actual Length (cm.) | Inner Diameter (cm.) |
|---|---|
| 22 | 0.172 |
| 23 | 0.174 |
| 24 | 0.176 |
| 25 | 0.178 |
| 26 | 0.180 |
| 27 | 0.181 |
| 28 | 0.183 |
| 29 | 0.185 |
| 30 | 0.186 |
| 31 | 0.188 |
| 32 | 0.189 |
| 33 | 0.191 |
| 34 | 0.192 |
| 35 | 0.193 |
| 36 | 0.195 |
| 37 | 0.196 |
| 38 | 0.197 |
| 39 | 0.199 |
| 40 | 0.200 |
| 41 | 0.201 |
| 42 | 0.202 | and implanting the venous catheter in the venous system of the patient.

13. The method of claim 12 in which said actual inner diameter is within 2 percent of the desired inner diameter.

14. The method of selecting and implanting a permanent venous catheter into a patient for use in chronic extracorporeal blood treatment procedures, which comprises: selecting a desired flow rate of 350 to 450 ml. per minute for a catheter to be implanted in a patient; selecting a permanent venous catheter having a actual length from the catheter distal tip to its integral, proximal end of 22–42 cm., said catheter having a lumen with an actual inner diameter within 3 percent of a desired inner diameter indicated in the Table below for the particular actual length:

| Actual Length (cm.) | Inner Diameter (cm.) |
|---|---|
| 22 | 0.185 |
| 23 | 0.187 |
| 24 | 0.189 |
| 25 | 0.191 |
| 26 | 0.193 |
| 27 | 0.195 |
| 28 | 0.197 |
| 29 | 0.198 |
| 30 | 0.200 |
| 31 | 0.202 |
| 32 | 0.203 |
| 33 | 0.205 |
| 34 | 0.206 |
| 35 | 0.208 |
| 36 | 0.209 |
| 37 | 0.211 |
| 38 | 0.212 |
| 39 | 0.214 |
| 40 | 0.215 |
| 41 | 0.216 |
| 42 | 0.218 | and implanting the venous catheter in the venous system of the patient.

15. The method of claim 14 in which said actual inner diameter is within 2 percent of the desired inner diameter.

16. The method of selecting and implanting a permanent venous catheter into a patient for use in chronic extracorporeal blood treatment procedures, which comprises: selecting a desired flow rate at least 450 ml. per minute for a catheter to be implanted in a patient; selecting a permanent venous catheter having an actual length from the catheter distal tip to its integral, proximal end of 22–42 cm., said catheter having a lumen with an actual inner diameter within 3 percent of a desired inner diameter indicated in the Table below for the particular actual length:

| Actual Length (cm.) | Inner Diameter (cm.) |
|---|---|
| 22 | 0.196 |
| 23 | 0.198 |
| 24 | 0.200 |
| 25 | 0.202 |
| 26 | 0.204 |
| 27 | 0.206 |
| 28 | 0.208 |
| 29 | 0.210 |
| 30 | 0.211 |
| 31 | 0.213 |
| 32 | 0.215 |
| 33 | 0.217 |
| 34 | 0.218 |
| 35 | 0.220 |
| 36 | 0.221 |
| 37 | 0.223 |
| 38 | 0.224 |
| 39 | 0.226 |
| 40 | 0.227 |
| 41 | 0.229 |
| 42 | 0.230 | and implanting the venous catheter in the venous system of the patient.

17. The method of claim 16 in which said actual inner diameter is within 2 percent of the desired inner diameter.

18. The method of selecting and implanting a permanent venous catheter into a patient for use in chronic extracorporeal blood treatment procedures, which comprises:

determining the Body Surface Area (BSA) of the patient;

selecting a permanent venous catheter having an actual length from the catheter distal tip to the point on the catheter where it is to penetrate the wall of a desired vein into which it is to be implanted, said actual length of the catheter being within 10% of a desired length as indicated below for the Body Surface Area (BSA) of the particular patient, and the particular vein through which the catheter is to extend (RJIV; RSCV; LIJV; or LSCV):

| BSA m² | RIJV cm | RSCV cm | LIJV cm | LSCV cm |
|---|---|---|---|---|
| 1.20 | 11.1 | 13.4 | 13.9 | 16.5 |
| 1.25 | 11.2 | 13.5 | 14.1 | 16.7 |
| 1.30 | 11.4 | 13.7 | 14.2 | 16.9 |
| 1.35 | 11.5 | 13.8 | 14.4 | 17.1 |
| 1.40 | 11.7 | 13.9 | 14.6 | 17.3 |
| 1.45 | 11.9 | 14.1 | 14.8 | 17.5 |
| 1.50 | 12.0 | 14.2 | 15.0 | 17.7 |
| 1.55 | 12.2 | 14.4 | 15.1 | 17.9 |
| 1.60 | 12.3 | 14.5 | 15.3 | 18.1 |
| 1.65 | 12.5 | 14.6 | 15.5 | 18.3 |
| 1.70 | 12.6 | 14.8 | 15.7 | 18.5 |
| 1.75 | 12.8 | 14.9 | 15.9 | 18.7 |
| 1.80 | 12.9 | 15.1 | 16.1 | 18.9 |
| 1.85 | 13.1 | 15.2 | 16.2 | 19.1 |
| 1.90 | 13.2 | 15.3 | 16.4 | 19.3 |
| 1.95 | 13.4 | 15.5 | 16.6 | 19.5 |

-continued

| BSA m² | RIJV cm | RSCV cm | LIJV cm | LSCV cm |
|---|---|---|---|---|
| 2.00 | 13.5 | 15.6 | 16.8 | 19.7 |
| 2.10 | 13.8 | 15.9 | 17.1 | 20.1 |
| 2.20 | 14.2 | 16.2 | 17.5 | 20.5 |
| 2.30 | 14.5 | 16.5 | 17.9 | 20.9 |
| 2.45 | 14.9 | 16.9 | 18.4 | 21.5 |
| 2.60 | 15.4 | 17.3 | 19.0 | 22.1 |
| 2.75 | 15.8 | 17.7 | 19.5 | 22.7 | and implanting the venous catheter in the venous system of the patient with the distal tip of the catheter being in or adjacent to the upper right atrium of the heart.

* * * * *